Figure 1:
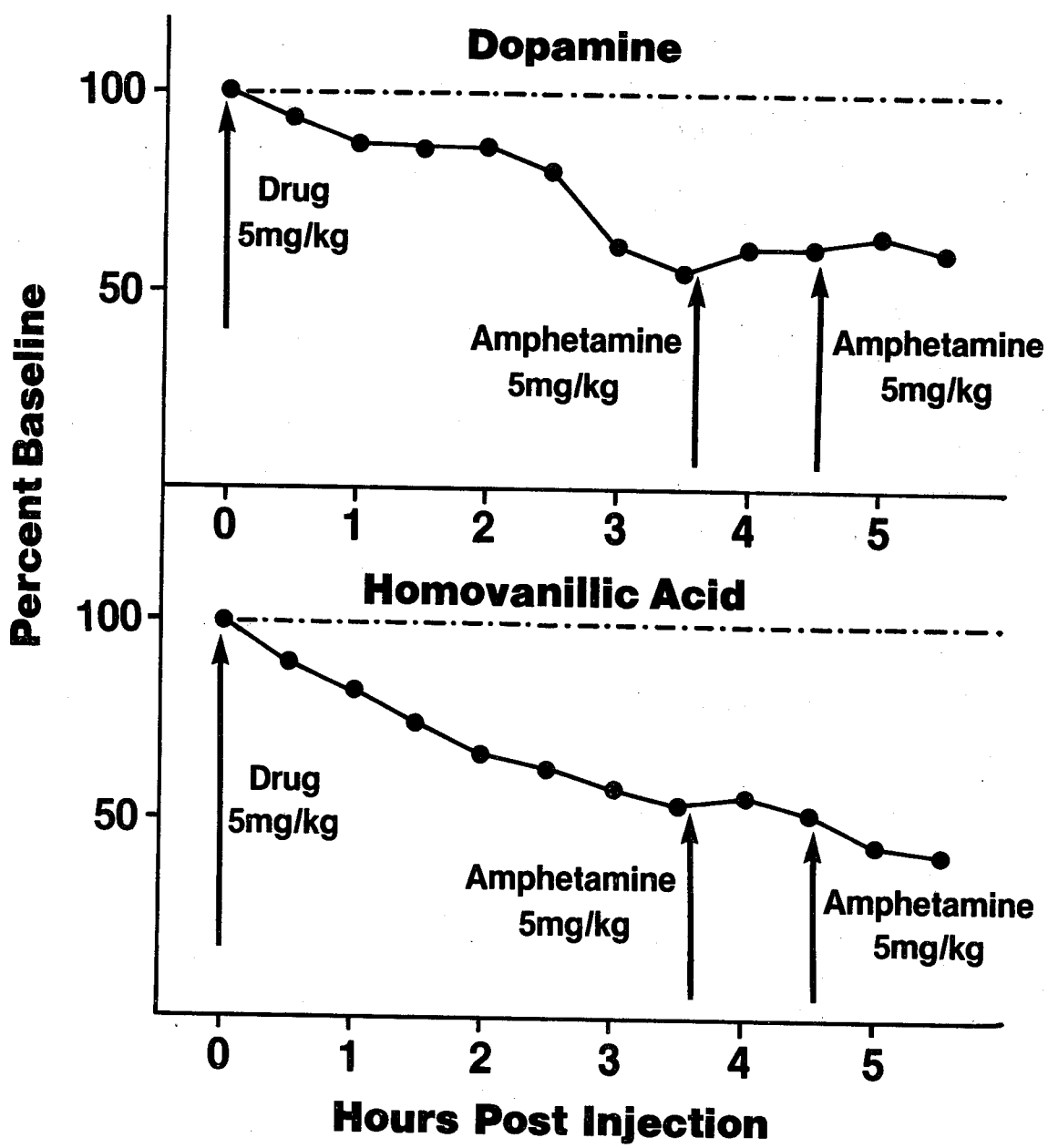

United States Patent [19]

Cassady et al.

[11] 4,378,368

[45] Mar. 29, 1983

[54] USE OF 4-(2-DI-N-PROPYLAMINOETHYL)INDOLE OR A SALT THEREOF AS A PRESYNAPTIC DOPAMINE AUTORECEPTOR STIMULANT

[75] Inventors: John M. Cassady, West Lafayette; James A. Clemens, Indianapolis, both of Ind.

[73] Assignees: Purdue Research Foundation, West Lafayette; Eli Lilly and Company, Indianapolis, both of Ind.

[21] Appl. No.: 318,093

[22] Filed: Nov. 4, 1981

[51] Int. Cl.³ ............................................. A61U 43/36
[52] U.S. Cl. ................................................... 424/274
[58] Field of Search ......................................... 424/274

[56] References Cited

FOREIGN PATENT DOCUMENTS 1344579 of 0000 France .

OTHER PUBLICATIONS

Cannon et al., J. Med. Chem., 24, 238–240, (1981).
Troxler et al., Helv. Chim. Acta., 51, 1616, (1968).

*Primary Examiner*—Stanley J. Friedman
*Attorney, Agent, or Firm*—James L. Rowe; Arthur R. Whale

[57] ABSTRACT

4-2-(di-n-propylaminoethyl)indole or a salt thereof is used to stimulate presynaptic dopamine autoreceptors in mammals.

2 Claims, 1 Drawing Figure

USE OF 4-(2-DI-N-PROPYLAMINOETHYL)INDOLE OR A SALT THEREOF AS A PRESYNAPTIC DOPAMINE AUTORECEPTOR STIMULANT

BACKGROUND OF THE INVENTION 4-(2-Dimethylaminoethyl)indole is disclosed by Hofmann and Troxler in French Pat. No. 1,344,579 and in Troxler et al., *Helv. Chim. Acta*, 51, 1616 (1968). Cannon et al. in *J. Med. Chem.*, 24, 238–40 (1981) describe 4-(2-di-n-propylaminoethyl)indole (also named as 4-(N,N-di-n-propyl 2-aminoethyl)indole).

SUMMARY OF THE INVENTION

This invention provides a method for stimulating presynaptic dopamine autoreceptors in the brain which comprises administering to a mammal having excessive dopamine release, a dopamine autoreceptor stimulating amount of 4-(2-di-n-propylaminoethyl)indole of structure

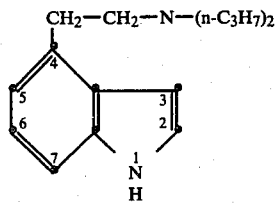

Drugs that stimulate dopamine autoreceptors are also called presynaptic dopaminergic agonists. The presynaptic dopaminergic activity of I was measured by using in vivo voltammetry to measure dopamine release. This electrochemical technique allows an observer to continuously monitor changes in dopamine release and the levels of one of its principal metabolites, homovanillic acid (HVA).

In this measurement system, using in vivo voltammetry, electrodes are implanted in the brains of anesthetized rats while the rats are held in a stereotaxic instrument. The same electrode configuration is used here as is used in the standard technique of electrochemical analysis. The working electrode (the one sensitive to dopamine and HVA) was made with carbon paste (a mixture of finely powdered graphite and mineral oil). The reference electrode was a silver-silver chloride wire and the auxillary electrode was a stainless steel screw.

The instrumentation consisted of a Princeton Applied Research model 174A polarographic analyzer. The output of the analyzer was semidifferentiated and displayed on an X-Y plotter. The working electrode was lowered into the corpus striatum, the reference electrode placed in the cerebral cortex and the auxillary electrode screwed into the skull. The voltage from the polarographic analyzer was varied linearly from 0 to +0.6 volts. When the oxidation potentials for dopamine and HVA were reached, an increase in current flow was observed. The amount of current flow is directly proportional to the amount of dopamine or HVA at the electrode tip. Using this method, changes in the release of dopamine and HVA in the corpus striatum were determined.

After a steady baseline had been established for dopamine and for HVA, 5.0 mg/kg of 4-(2-N,N-di-n-propylaminoethyl)indole was given by i.p. injection as an aqueous suspension. Dopamine and HVA levels were measured at 30 minute intervals. At about 3.5 hours, amphetamine (5 mg/kg, i.e.) was given to determine if the compound under test reduced dopaminergic function to the extent that a dopamine releaser like amphetamine could be blocked.

FIG. 1 shows that, after injection of 5 mg/kg of 4-(2-N,N-di-n-propylaminoethyl)indole, both dopamine and HVA release were significantly reduced and the ability of amphetamine to produce a large rise in dopamine was blocked.

The above experiment demonstrated that 4-(2-di-N-propylaminoethyl)indole was a presynaptic dopaminergic drug. Since it seemed desirable to find a selective presynaptic dopaminergic drug, the post-synaptic activity of the drug was determined. Compounds with central post-synaptic dopaminergic activity affect turning behavior in a test procedure utilizing 6-hydroxydopamine-lesioned rats. In this test, nigro-neostriatal-lesioned rats, prepared by the procedure of Ungerstedt and Arbuthnott, *Brain Res*, 24, 485 (1970) are employed. A compound having postsynaptic dopamine agonist activity, upon injection, causes the rats to turn in circles contralateral to the side of the lesion. After a latency period, which varies from compound to compound, the number of turns is counted over a 15-minute period.

4-(2-Di-n-propylaminoethyl)indole administered in water I.P. at a 5 mg/kg dose to 5 rats gave an average of 12.1 contralateral turns during the first hour after administration. This degree of turning is considered to be insignificant or at best very weak. In addition, the rats showed no stereotyped behavior, another measure of central postsynaptic activity.

The above results indicate that 4-(2-di-n-propylaminoethyl)indole acts primarily at presynaptic dopamine autoreceptors to reduce dopamine release, while its postsynaptic effects are extremely weak or non-existant. Thus, it appears that this compound possesses a high degree of selectivity for presynaptic dopamine autoreceptors.

The pharmaceutically-acceptable acid addition salts of 4-(2-di-n-propylaminoethyl)indole useful in the process of this invention include salts derived from inorganic acids such as: hydrochloric acid, nitric acid, phosphoric acid, sulfuric acid, hydrobromic acid, hydriodic acid, nitrous acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Dopamine autoreceptor stimulants may be useful in human medicine. Current evidence indicates that neuroleptic drugs exert their beneficial effect in schizophrenia by blocking the action of dopamine on its postsynaptic receptor. The compound of this invention could be anticipated to be useful as a neuroleptic merely by decreasing dopamine release. The reduction in dopamine release should have the same net effect as blockade of dopamine receptors. In addition, a dopamine autoreceptor stimulant may possess advantages over the currently-available neuroleptics, because most known neuroleptics produce side effects that appear to be related to long-term blockade of postsynaptic dopamine receptors (Parkinson-like symptoms and tardive dyskinesia) which long-term blockade should be lacking with 4-(2-di-n-propylaminoethyl)indole or one of its salts.

4-(2-di-n-Propylaminoethyl)indole is prepared according to the procedure set forth in Flow Chart 1 below.

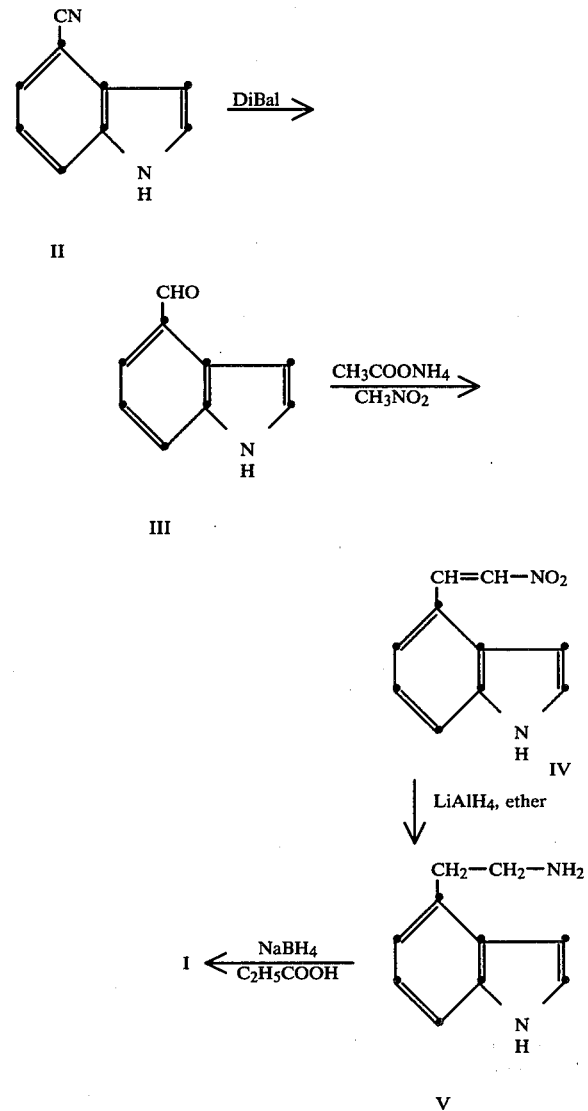

Flow Chart I

According to Flow Chart 1, 4-cyanoindole (II) prepared by the method of Uhle, *J.A.C.S.*, 71, 761 (1949) is converted to 4-formylindole (III) with diisobutylaluminum hydride (DiBAl). Condensation of the 4-formyl derivative with nitromethane in the presence of ammonium acetate yields 4-(2-nitroethenyl)indole (IV). Reduction of IV with LiAlH₄ in ether gives 4-(2-aminoethyl)indole (V). (This synthetic route is based on that of Troxler et al. *Helv. Chim. Acta*, 51, 1616 (1968)). Reductive alkylation of the primary amine with NaBH₄ and propionic acid produces the compound of this invention (I).

The following specific example further exemplifies the procedure of Flow Chart I.

EXAMPLE 1

Preparation of 4-(2-Di-n-propylaminoethyl)indole

Two grams of 4-cyanoindole, prepared by the method of Uhle *J.A.C.S.*, 71, 761 (1949), were dissolved in 20 ml of anhydrous ether. 15 Milliliters of a 20% solution of diisobutylaluminum hydride (DiBAl) in hexane were added in dropwise fashion. The reaction mixture was stirred at room temperature for about 30 minutes and then heated to refluxing temperature for about three hours. The reaction mixture was then cooled and 10 ml of a 4:1 dioxane-water solution added with stirring over a period of five minutes. 30 Milliliters of 1 N HCl were added over a 30 minute period with stirring. The aqueous mixture was extracted with several portions of ethyl acetate and the ethyl acetate extracts combined. The combined extracts were washed with 10 percent aqueous sodium carbonate and with saturated aqueous sodium chloride and were then dried. Evaporation of the solvent yielded 2.24 g of 4-formylindole. 4-Formylindole was purified by chromatography over Florisil using a hexane-ether solvent mixture (2:1) as the eluant. Recrystallization of the chromatographed 4-formylindole from an ether-hexane solvent mixture yielded yellow needles of 4-formylindole melting at 136°–137° C. Infrared spectrum; peak at 1670 cm$^{-1}$; nmr (D₆ acetone) δ 10.35 (s, 1H, C$\underline{H}$O), 7.2–7.9 (m, 6H, Ar.); mass spectrum; molecular ion at 145.

A mixture of 210.7 mg of 4-formylindole and 2.1 ml of nitromethane plus 60 mg of ammonium acetate as a catalyst was heated at about 110° C. for about two hours. The reaction mixture was then poured into water and the aqueous mixture thoroughly extracted with ethyl acetate. The combined ethyl acetate extracts were washed with water and then dried. Evaporation of the ethyl acetate yielded 295 mg of an orange-colored solid which, after recrystallization from methanol, yielded 240 mg of dark rust-colored leaves of 4-(2-nitroethenyl)indole melting at 152°–4° C. with decomposition; nmr; δ 6.9–8.7 (m, 8H, Ar., NH, olefinic); infrared spectrum; λ=3300 cm$^{-1}$; mass spectrum; molecular ion at 188.

A solution was prepared by dissolving 751.1 mg of 4-(2-nitroethenyl)indole in a minimum amount of anhydrous THF. This solution was added in dropwise fashion to a stirred solution containing 3 g of lithium aluminum hydride and 30 ml of anhydrous ether. The solution was heated to refluxing temperature for three hours and then stirred at ambient temperature overnight. The reaction mixture was then slowly quenched by the addition of water. The reaction mixture was filtered to remove inorganic salts and the filtrate was extracted with ether. The ether extract was dried and ether removed therefrom by evaporation to yield 577 mg of a tan solid melting at 91°–3° C. comprising 4-(2-aminoethyl)indole. The compound had the following physical characteristics: nmr; δ 9.5 (bs, 1H, NH); 6.6–7.5 (m, 5H, Ar); 3.1 (bs, 4H, C$\underline{H}_2$—CH$_2$); 1.45 (bs, 2H, N$\underline{H}_2$); mass spectrum; molecular ion at 160.

About 30 millimoles of sodium borohydride were added to a solution of 90 millimoles of propionic acid and 20 ml of benzene while maintaining the temperature at about 20° C. After the evolution of gas had ceased (about one hour), 6 millimoles of 4-(2-aminoethyl)indole were added and the resulting reaction mixture heated to refluxing temperature for about three hours. The reaction mixture was then cooled and shaken with 2 N aqueous sodium hydroxide.

The organic layer was separated and dried and the solvents removed therefrom by evaporation yielding as a residue 4-(di-n-propylaminoethyl)indole plus 4-(N-propionyl-2-aminoethyl)indole. The mixture was separated by chromatography on alumina preparative tlc plates with chloroform as the eluant. 4-(Di-n-propyl-2-aminoethyl)indole thus purified melted at about 79° C. nmr; δ 8.6 (bs, 1H, NH); 6.6–7.4 (m, 6H, Ar); 3.0 (bs, 4H, Ar—CH$_2$—CH$_2$N) 2.6 (t, 4H, N—(CH$_2$C$\underline{H}_2$CH$_3$)$_2$); 1.6 (m, 4H, N—(CH$_2$C$\underline{H}_2$CH$_3$)$_2$); 0.9 (t, 6H, (C$\underline{H}_3$)$_2$); mass spectrum; molecular ion at 244, other maxima at 144, 130, 114.

In using 4-(2-di-n-propylaminoethyl)indole as a stimulator of presynaptic dopamine autoreceptors (as a presynaptic dopaminergic drug), the compound or a pharmaceutically-acceptable acid addition salt is administered to a patient in need of decreasing excessive dopamine release in an amount sufficient to stimulate presynaptic dopamine autoreceptors.

Oral administration is preferred. If parenteral administration is used, the injection is preferably by the subcutaneous route using an appropriate pharmaceutical formulation. Other modes of parenteral administration such as intraperitoneal, intramuscular, or intravenous routes are equally effective. In particular, with intravenous or intramuscular administration, a water soluble pharmaceutically-acceptable salt is employed. For oral administration, the compound either as the free base or in the form of a salt thereof, can also be mixed with standard pharmaceutical excipients and loaded into empty telescoping gelatin capsules or pressed into tablets. The oral dosage range is from about 0.01 to 10 mg./kg. of mammalian weight and the parenteral dose range from about 0.0025 to 2.5 mg./kg. Oral unit dosage forms may thus contain from 0.5 to 250 mg. and the dosage may be repeated 2 to 4 times per day. Parenteral dosage forms should contain from 0.1 to 100 mg. of active drug.

We claim:

1. A method of stimulating presynaptic dopamine autoreceptors in a mammalian brain in which there is excess dopamine release which needs to be decreased which comprises administering to said mammal a presynaptic dopamine autoreceptor stimulating amount of 4-(2-di-n-propylaminoethyl)indole at a pharmaceutically-acceptable salt thereof.

2. A process according to claim 1 in which from 0.01 to 10 mg/kg orally or 0.0025 to 2.5 mg/kg parenterally of 4-(2-di-n-propylaminoethyl)indole is administered per day.

* * * * *